United States Patent [19]

Sibrava

[11] 4,205,549
[45] Jun. 3, 1980

[54] APPARATUS FOR PREPARING A LIQUID SAMPLE

[75] Inventor: Joseph Sibrava, Fairfield, Conn.

[73] Assignee: The Perkin-Elmer Corporation, Norwalk, Conn.

[21] Appl. No.: 894,512

[22] Filed: Apr. 7, 1978

[51] Int. Cl.² ............................................. B21J 13/00
[52] U.S. Cl. ....................................... 72/448; 72/458; 72/427
[58] Field of Search ................. 72/423, 344, 367, 448, 72/369, 458, 427

[56] References Cited

U.S. PATENT DOCUMENTS

| 617,277 | 1/1899 | Campbell | 72/344 |
|---|---|---|---|
| 808,177 | 12/1905 | Thiem | 72/367 X |
| 1,118,372 | 11/1914 | Shrum | 72/367 |
| 1,393,916 | 10/1921 | Smith | 72/427 X |
| 2,275,220 | 3/1942 | Emkur | 72/367 X |
| 2,634,576 | 4/1953 | Siebel | 72/427 X |

Primary Examiner—Leon Gilden
Attorney, Agent, or Firm—S. A. Giarratana; F. L. Masselle; E. T. Grimes

[57] ABSTRACT

Method and apparatus for preparing a liquid sample for combustion and analysis in an elemental analyzer. In order to avoid damage to the quartz combustion tube and ladle by molten aluminum, the sample is placed in an aluminum foil vial which is crimped and placed in turn in an open ended capsule of nickel or other non-reactive metal. The capsule is then distorted by a novel encapsulator to partially obstruct the open end and retain the liquid sample vial therein during the combustion process.

3 Claims, 12 Drawing Figures

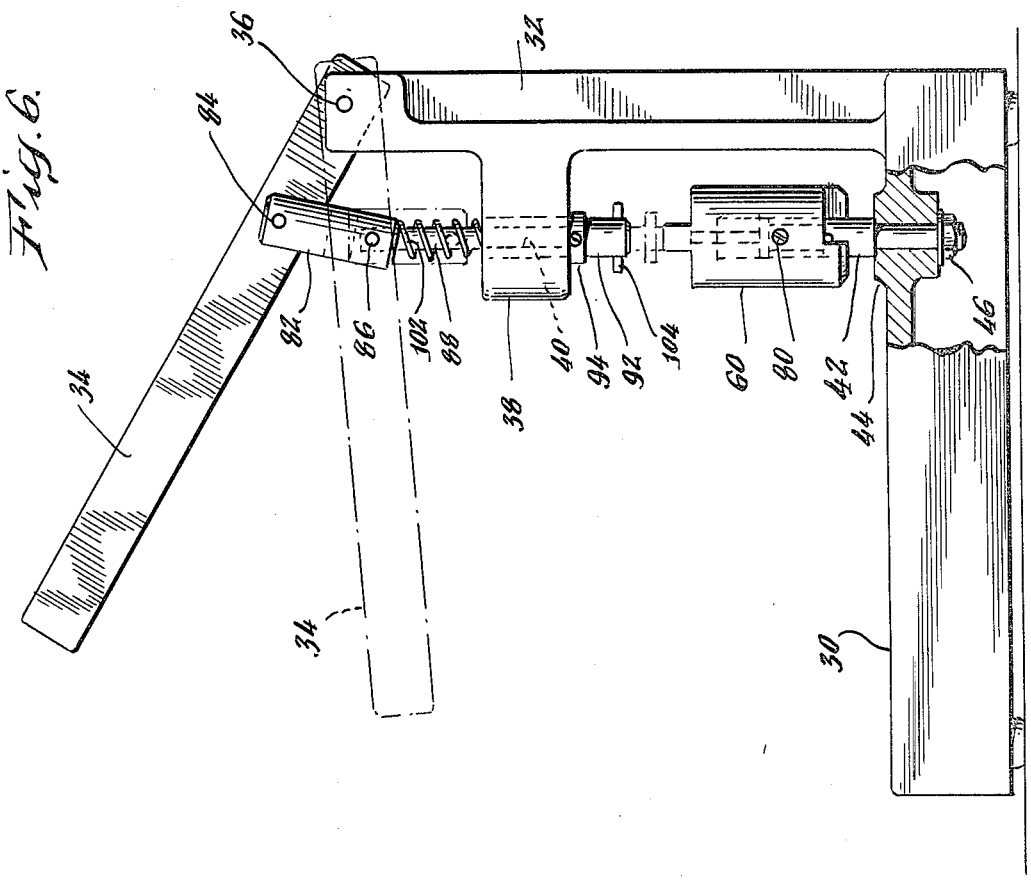
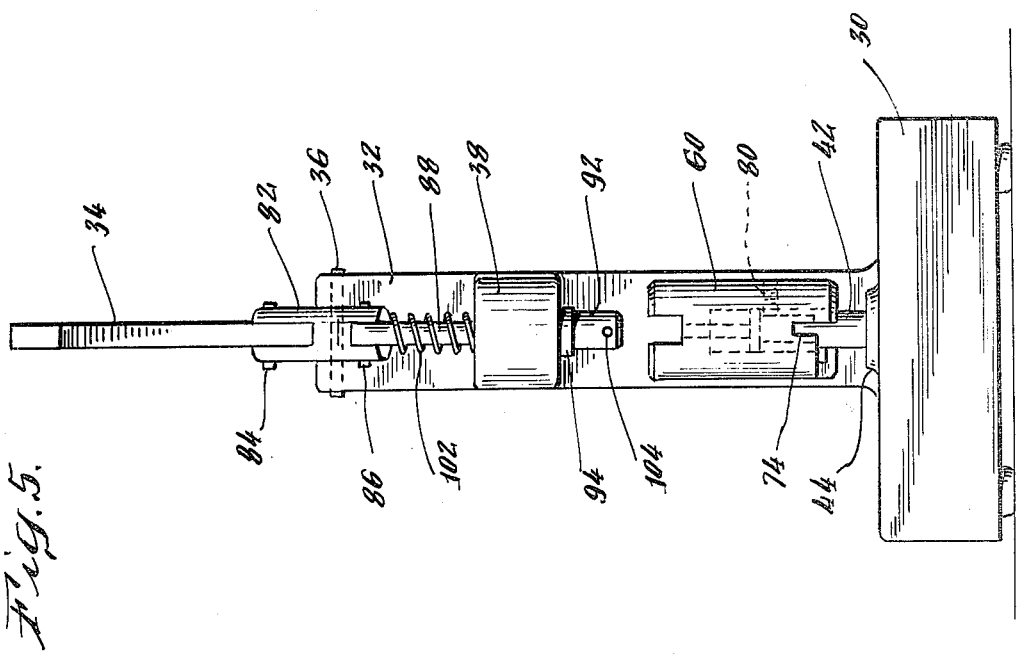

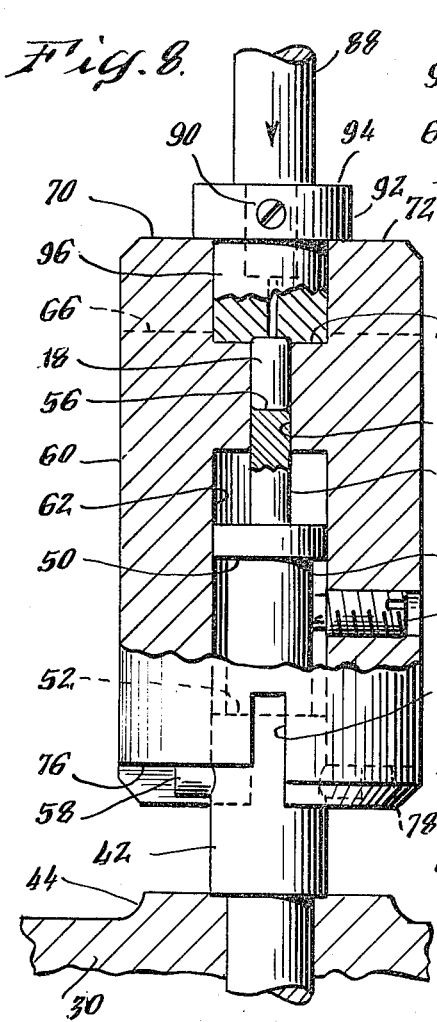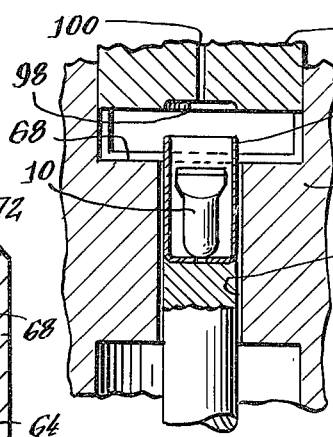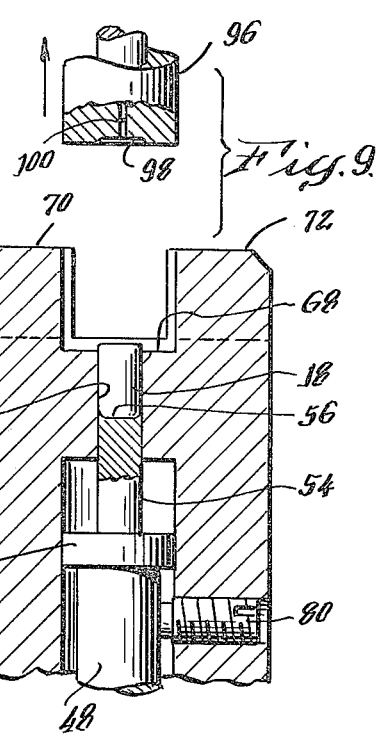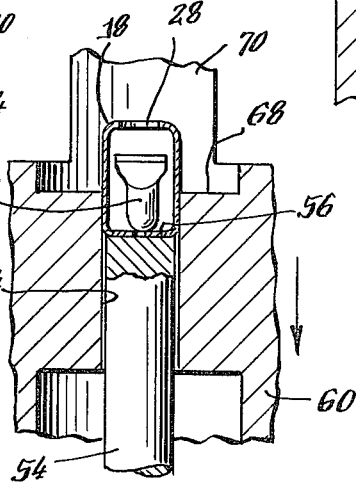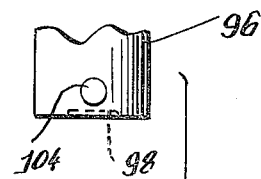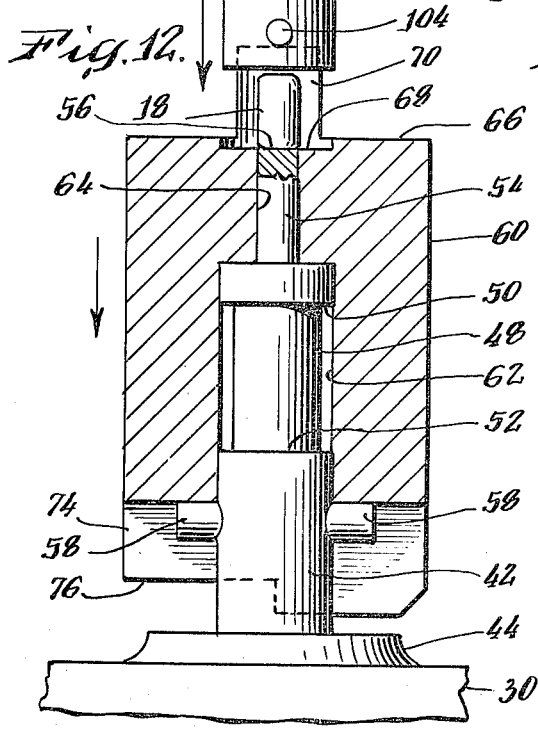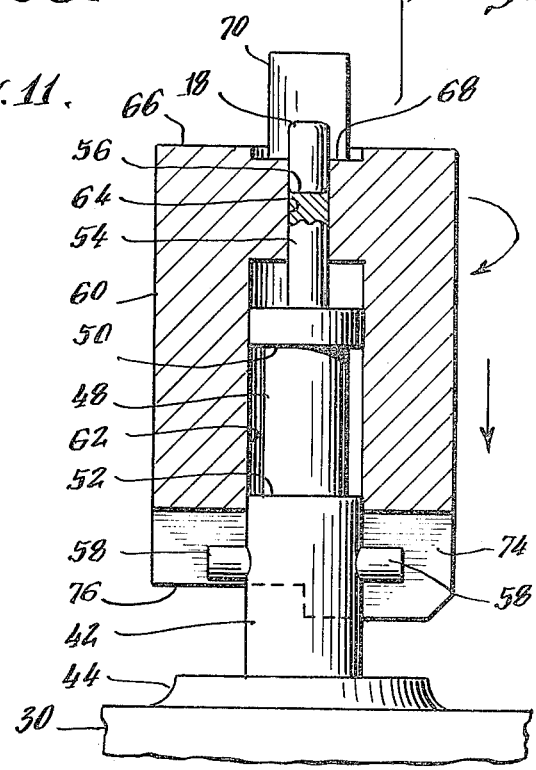

APPARATUS FOR PREPARING A LIQUID SAMPLE

BACKGROUND OF THE INVENTION

In U.S. Pat. No. 4,055,259 there is disclosed an apparatus for transporting small solid samples into the combustion chamber of an elemental analyzer. Analyzers of this type normally combust a sample at a very high temperature (1000° C.) in an oxygen atmosphere. The products of combustion are then analyzed to detect the presence and amount of particular elements, primarily carbon, hydrogen, and nitrogen. As disclosed in that patent, solid samples are usually placed within capsules of platinum or other non-reactive metals for subsequent combustion.

When dealing with liquid samples, certain unique problems arise due to the fact that the samples, which may be highly volatile, must be sealed and contained prior to combustion. Such samples may be successfully contained within an aluminum foil vial which is thereafter sealed by crimping. Upon exposure to combustion temperatures, the aluminum melts or oxidizes releasing the liquid for combustion. The problem, however, is that the aluminum must be kept from contact with the quartz tube of the combustion chamber or with the quartz ladle which is employed to insert the foil vial. This is because the quartz is damaged by the molten aluminum and, when this occurs, the only remedy is to replace the quartz. This is expensive and results in extended down time of the analyzer. One method which has been employed to overcome this problem involves the use of a "boat" of non-reactive metal. The boat, however, occasionally tips, spilling the sample.

Accordingly, it is a primary object of the present invention to provide a method for preparing a liquid sample which overcomes the disadvantages set forth above. Another object of the present invention is to provide an apparatus useful in carrying out such method.

SUMMARY OF THE INVENTION

The invention comprises a method of preparing a liquid sample for introduction into a combustion chamber by providing a substantially cylindrical metal foil vial having a closed end and an open end. The liqu'd sample is introduced into the vial which is then crimped at its open end. A substantially cylindrical metallic capsule is provided which is larger than the foil vial and has a closed end and an open end, the closed end defining a small hole to permit gas passage therethrough. The foil vial is placed within the capsule with the crimped end of the vial near the open end of the capsule. The capsule is then distorted to partially obstruct its open end to retain the liquid vial therein.

In carrying out the method of this invention, there is provided an apparatus for forming the end of the cylindrical metal capsule. The apparatus includes a base and a vertical post extending upwardly from the base and terminating in a capsule supporting end. A capsule containment member, which defines a cylindrical passage therethrough, slidably engages the post. Means are provided for selectively supporting the containment member in either a raised, capsule-enclosing, position or a lowered, capsule-releasing, position. A capsule end forming tool is supported by the base for vertically reciprocating movement to engage a capsule enclosed within the containment member. Means are provided for selectively moving the tool into and out of engagement with an enclosed capsule.

BRIEF DESCRIPTION OF THE DRAWINGS

FIG. 5 is a front elevation of an encapsulating tool in accordance with the invention;

FIG. 6 is a side elevation of the encapsulator of FIG. 5, partially broken away to illustrate its internal construction and illustrating two operative positions by means of dash-dotted lines;

FIG. 7 is an enlarged cross section of the working portion of the encapsulator of FIGS. 5 and 6 showing the manner in which a capsule is placed therein;

FIG. 8 is an enlarged cross-sectional view illustrating the operation of the encapsulator to distort the capsule end;

FIG. 9 illustrates the separation of the working parts when encapsulation is completed;

FIG. 10 illustrates the capsule containment member rotated to facilitate discharge of the capsule;

FIG. 11 illustrates the containment member during the process of capsule release; and, FIG. 12 illustrates the containment member fully depressed and the completed capsule released.

DESCRIPTION OF THE PREFERRED EMBODIMENT

Figure 1:
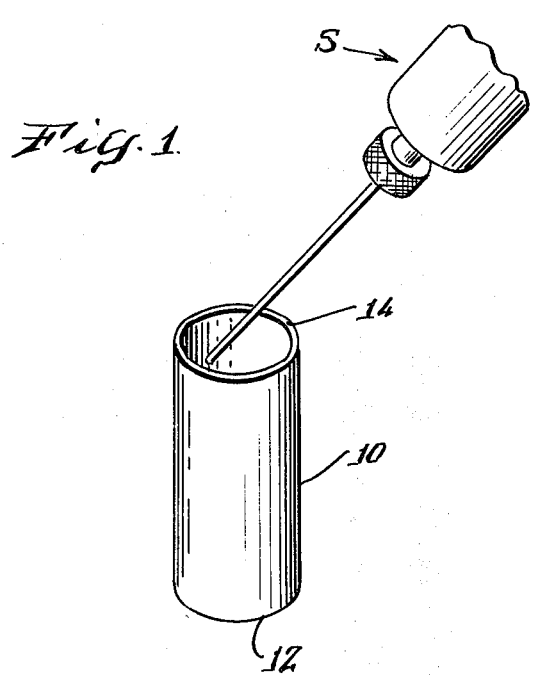
FIG. 1 is a perspective view illustrating the loading of a liquid sample into a metal foil vial by means of a syringe.
Figure 2:
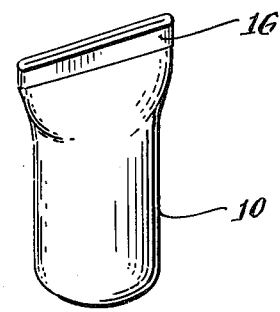
FIG. 2 illustrates the liquid containing vial of FIG. 1 after being crimped and sealed.

With particular reference to FIG. 1, there is illustrated a metal foil vial 10 in the process of receiving a liquid sample by means of a syringe S. Vial 10 is basically cylindrical and has a closed convex bottom 12 and an open top 14. It is quite small and may have, for example, a capacity of approximately 3 microliters. After receiving the sample liquid, the vial is closed and sealed by means of a crimp 16, as shown in FIG. 2. This may be done by a crimping tool of a type well known in the art. As will be apparent from FIG. 2, the crimped portion 16 of the vial 10 is longer than the diameter of the cylindrical sidewall of the vial.

Figure 3:
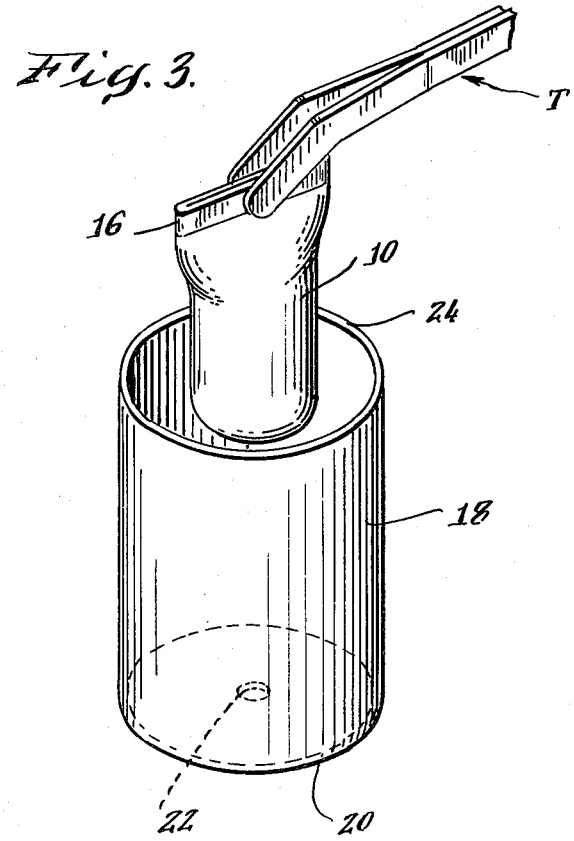
FIG. 3 illustrates the sealed vial of FIG. 2 being placed within a non-reactive metallic capsule.
Figure 4:
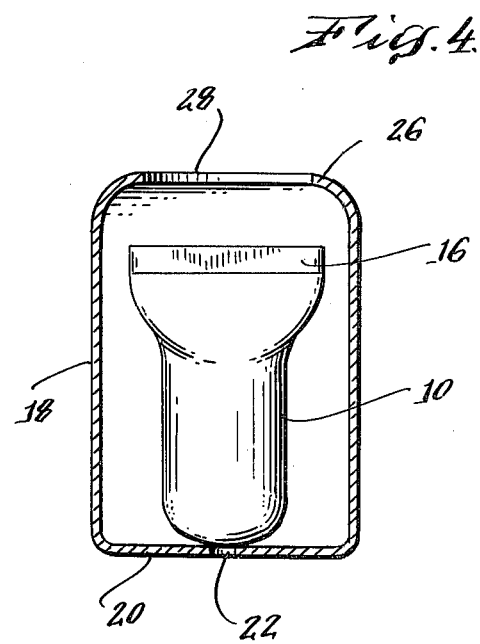
FIG. 4 is an elevational cross section through the loaded capsule of FIG. 3 after distortion and partial closing of its open end.

There is next provided a capsule 18 as shown in FIG. 3. Capsule 18 is made of a substantially non-reactive metal, such as nickel or platinum. It, too, is cylindrical but large enough to receive the crimped vial 10 therein. It has a bottom wall 20 which defines a small, axial gas passage 22 therethrough. Its upper end 24 is open. Through this upper end, the loaded vial 10 is inserted by means of tweezers T. Finally, the upper end of the loaded capsule is deformed or "rolled" as shown in FIG. 4 to form an encircling shoulder 26 defining an upper opening 28 having too small a diameter to permit the crimped vial 10 to pass therethrough.

The capsule 18, having the loaded vial 10 therein, is loaded into the combustion tube of an analyzer instrument in the usual manner, such as, for example, as taught in the aforementioned patent. Flushing gas, oxygen, and products of combustion are afforded free passage through the length of the capsule due to the presence of the gas passage 22 and opening 28. The high temperature within the combustion chamber substantially destroys the aluminum vial 10 by melting and oxidation but its remains are kept within the capsule. The liquid, however, is combusted and its products are swept into the analysis portion of the instrument, as is well known to those versed in the art.

The tool which is employed to distort the end of the capsule 18 is illustrated in FIGS. 5–12. As may be seen in FIGS. 5 and 6, it comprises a substantially horizontal base 30 with a vertically extending column 32 supporting at its upper end a lever arm 34 by means of a pivot 36. Extending outwardly over the base 30 from the column 32 near its upper end is a guide 38 which defines a vertical guideway and bearing 40 therein.

Mounted to, and extending upwardly from, the base 30 is a guide post 42 axially aligned with the bearing 40 in guide 38. As will be seen in FIG. 6, the lower end of the guide post 42 extends through a boss 44 in the base 30 where it is secured by a nut 46. Guide post 42 is best illustrated in FIGS. 8 and 12. As will be seen therein, it includes a turned down portion 48, thereby forming upper 50 and lower 52 shoulders. The upper end of the post 42 is further reduced to form a pin 54 which, at its uppermost end, has a slightly concave surface 56. Post 42 is drilled below the lower shoulder 52 to receive a pin 58 which extends diametrically therethrough and protrudes on either side of the post 42 as seen in the drawings.

Surrounding and enclosing the upper end of the post 42 is a substantially cylindrical capsule containment member 60. The capsule containment member 60 is vertically slidable upon the post 42 by means of an axial bore having a larger diameter portion 62 which is slidable on the larger diameter portions of post 42. An upper, small diameter, portion 64 of the bore extends through the upper surface 66 of member 60, where it is surrounded by a circular recess 68.

Extending upwardly from the upper surface 66 on either side of the recess 68, are a pair of diametrically opposed shoulders 70, 72. The inside surfaces of shoulders 70, 72 are curved to form partial cylindrical sidewalls extending upwardly from the recess 68.

Formed in the lower end of the member 60 is a diametrical slot 74 of sufficient width to receive the pin 58 therein. Also formed in the bottom of the member 60 are a pair of opposed recesses 76, 78, each of which extends through a 90° arc on the bottom of member 60 and communicates with a different end of the slot 74. The sidewall of the member 60 is drilled and tapped to receive a set screw 80 which normally extends into the turned down portion 48 of the post 42 to thereby limit the vertical movement of the capsule containment member 60.

Returning now to FIGS. 5 and 6, it will be noted that a link member 82, bifurcated at its two ends, is secured by means of a first pivot 84 to lever arm 34 and by a second pivot 86 to a vertically depending rod 88 for longitudinal movement within the bearing 40 of guide 38. Mounted on the lower end of the rod 88 by means of a screw 90 is a capsule forming tool 92. Tool 92 includes a circumferential flange 94, and a depending cylindrical ram 96 positioned to slidably engage the cylindrical inner surfaces of shoulders 70, 72 and enter recess 68. The lower, working, surface of ram 96 is substantially planar but includes a central recess 98 of approximately the same diameter as the small diameter bore portion 64 of member 60. A small air release passage 100 extends upwardly from the recess 98.

Referring back to FIGS. 5 and 6, a compression spring 102 will be seen to extend between the guide 38 and the link member 82, thereby tending to maintain the lever 34 in its raised position, the upward movement being limited by the flange 94 on tool 92. Extending diametrically through ram 96 and outwardly from opposite sides thereof is a pin 104.

OPERATION

The operation of the apparatus of this invention will now be explained with particular reference to FIGS. 7–12.

The capsule containment member 60 is lifted on the post 42 and rotated to its raised position shown in FIG. 8, wherein the bottom recesses 76, 78 rest upon pin 58. In this position, the small diameter bore 64 of the containment member 60 extends above the concave surface 56 of pin 54. The capsule 18 of FIG. 3 is placed into this bore as shown in FIG. 7 where it rests upon concave surface 56 of pin 54.

Lever arm 34 is then lowered and the ram 96 descends between the shoulders 70, 72, the ends of pin 104 being positioned intermediate shoulders 70, 72. The recess 98 engages the upper end of the capsule 18 and crimps it inwardly as previously shown in FIG. 4. The lever arm 34 is then released and spring 102 retracts ram 96, as shown in FIG. 9.

In order to release the formed capsule 18, capsule containment member 60 is rotated 90° as illustrated in FIG. 10. In this position, the pin 58 in post 42 is aligned with the ends of slot 74 in member 60. This would normally permit the member 60 to return by gravity to the lowered position illustrated in FIG. 12. However, the compression of the capsule 18 will normally cause it to expand slightly and snugly engage the containment member. In order to release the capsule, tool 92 is lowered once again by means of the lever arm 34. However, as the containment member has now been turned 90°, the pin 104 on the tool is now aligned with and engages the shoulders 70, 72. This forces the containment member 60 downwardly on post 42, as shown in FIG. 12, thereby releasing the capsule 18 which can then be removed.

It is believed that the many advantages of this invention will now be apparent to those skilled in the art. It will also be understood that a number of variations and modifications may be made therein without departing from its spirit and scope. Accordingly, the foregoing description is to be construed as illustrative only, rather than limiting. This invention is limited only by the scope of the following claims.

I claim:

1. Apparatus for forming the end of a cylindrical metallic capsule to enclose therein a sample containing vial which comprises:
    a base;
    a post extending from said base and terminating in a capsule supporting end;
    a capsule containment member defining a cylindrical passage therethrough slidably engaging said post for movement between first and second elevations relative to said post;
    means for selectively supporting said containment member in either a capsule-enclosing position at said first elevation or a capsule-releasing position at said second elevation;

a capsule end forming tool supported by said base for reciprocating movement to engage a capsule enclosed within said containment member when in its first elevation;

said containment member and said tool being relatively rotatable about the axis of said cylindrical passage between first and second arcuate relationships, said tool being engageable with an enclosed capsule in said first arcuate relationship and when said containment member lies in its first elevation to form the capsule and engageable with said containment member in said second arcuate relationship to displace said containment member from said first elevation toward said second elevation; and means for selectively moving said tool into and out of engagement with an enclosed capsule in said containment member.

2. The apparatus of claim 1 wherein said containment member is rotatable about said post between said first and second arcuate relationships.

3. The apparatus of claim 2 wherein said post includes a horizontally projecting pin and the bottom of said containment member defines recesses cooperating with said pin to establish said first and second elevations and said first and second arcuate relationships.

* * * * *